US010751486B2

(12) United States Patent
Haverman et al.

(10) Patent No.: US 10,751,486 B2
(45) Date of Patent: Aug. 25, 2020

(54) USE OF INFRARED LIGHT ABSORPTION FOR VEIN FINDING AND PATIENT IDENTIFICATION (71) Applicant: Becton, Dickinson and Company, Franklin Lakes, NJ (US)

(72) Inventors: Yuri Haverman, Franklin Lakes, NJ (US); Oliver Crespo Diaz, Santa Clara, CA (US); Alan Wayne Fiedler, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 322 days.

(21) Appl. No.: 15/783,255

(22) Filed: Oct. 13, 2017

(65) Prior Publication Data

US 2018/0140784 A1 May 24, 2018

Related U.S. Application Data (60) Provisional application No. 62/424,236, filed on Nov. 18, 2016.

(51) Int. Cl.
*G06K 9/00* (2006.01)
*A61M 5/42* (2006.01)
(Continued)

(52) U.S. Cl.
CPC ........... *A61M 5/427* (2013.01); *A61B 5/0075* (2013.01); *A61B 5/0077* (2013.01); *A61B 5/1171* (2016.02); *A61B 5/489* (2013.01); *A61B 5/743* (2013.01); *A61B 5/745* (2013.01); *G06K 9/00671* (2013.01); *G06K 9/00885* (2013.01); *G06K 9/2018* (2013.01); *G16H 10/60* (2018.01);
(Continued)

(58) Field of Classification Search
CPC . A61M 5/427; A61M 2205/583; A61B 5/489; A61B 5/0075; G06F 19/30
See application file for complete search history.

(56) References Cited

U.S. PATENT DOCUMENTS 3,667,464 A * 6/1972 Alligood, Jr. ........ A61M 5/1411
604/254
4,832,690 A * 5/1989 Kuu .................... A61M 5/1409
604/520

(Continued)

FOREIGN PATENT DOCUMENTS

WO WO 2006/061169 A1 6/2006
WO WO 2017/060281 A1 4/2017

OTHER PUBLICATIONS

Extended European Search report dated Apr. 3, 2018, in European Patent Application No. EP 17198895.9.

*Primary Examiner* — Amir Alavi
(74) *Attorney, Agent, or Firm* — Knobbe Martens Olson & Bear, LLP (57) ABSTRACT A medical system is capable of displaying and recording injection sites of patients. After patient identification based on the patient's vein patterns, the system can retrieve and display previous injection sites (e.g., for blood draw or injection) of the patient as overlaid at actual positions of the injection sites. The system can determine potential new injection sites based on the locations of the previous injection sites. The system can also ensure workflow compliance by displaying and tracking procedures performed by the healthcare professional.

11 Claims, 5 Drawing Sheets

(51) Int. Cl.
   *A61B 5/00*     (2006.01)
   *G16H 20/17*    (2018.01)
   *A61B 5/1171*   (2016.01)
   *G06K 9/20*     (2006.01)
   *G16H 10/60*    (2018.01)
   *G06F 19/00*    (2018.01)

(52) U.S. Cl.
   CPC ....... *G16H 20/17* (2018.01); *A61M 2205/583* (2013.01); *G06F 19/30* (2013.01); *G06K 2009/00932* (2013.01)

(56) References Cited

U.S. PATENT DOCUMENTS

| | | | |
|---|---|---|---|
| 5,049,129 A * | 9/1991 | Zdeb | A61M 5/1409 |
| | | | 141/309 |
| 5,116,316 A * | 5/1992 | Sertic | A61M 5/16827 |
| | | | 604/123 |
| 5,290,248 A * | 3/1994 | Bierman | A61M 39/1011 |
| | | | 604/174 |
| 5,423,753 A * | 6/1995 | Fowles | A61M 5/1409 |
| | | | 604/413 |
| 5,484,406 A * | 1/1996 | Wong | A61J 1/2089 |
| | | | 141/114 |
| 6,301,375 B1 | 10/2001 | Choi | |
| 8,348,896 B2 * | 1/2013 | Wagner | A61M 5/14546 |
| | | | 604/118 |
| 8,463,364 B2 * | 6/2013 | Wood | A61B 5/0064 |
| | | | 600/407 |
| 10,188,791 B2 * | 1/2019 | Burkholz | A61B 5/15003 |
| 2005/0283123 A1 * | 12/2005 | Lyde | A61M 5/40 |
| | | | 604/254 |
| 2007/0012322 A1 | 1/2007 | Ragg | |
| 2008/0045841 A1 | 2/2008 | Wood et al. | |
| 2011/0125028 A1 | 5/2011 | Wood et al. | |
| 2011/0301500 A1 | 12/2011 | Maguire et al. | |
| 2012/0127157 A1 | 5/2012 | Adler et al. | |
| 2013/0325493 A1 | 12/2013 | Wong et al. | |
| 2014/0039309 A1 | 2/2014 | Harris | |
| 2014/0379358 A1 | 12/2014 | Chovanda | |
| 2015/0306340 A1 | 10/2015 | Giap et al. | |
| 2018/0140784 A1 * | 5/2018 | Haverman | A61B 5/0075 |

\* cited by examiner

USE OF INFRARED LIGHT ABSORPTION FOR VEIN FINDING AND PATIENT IDENTIFICATION

RELATED APPLICATIONS

The present application claims priority under 35 U.S.C. § 119(e) to U.S. Provisional Application No. 62/424,236, filed on Nov. 18, 2016. The content of this related application is herein expressly incorporated by reference in its entirety.

BACKGROUND OF THE INVENTION

Field of the Invention

The invention relates generally to the field of medical workflow compliance, and more particularly to methods and systems for injection site identification and tracking.

Description of the Related Art

Prior to an injection or biological sample collection, such as a blood draw, a healthcare professional normally confirms the identity of the patient. Confirming the patient's identity can include obtaining an external confirmation of the patient. For example, the healthcare professional may verbally confirm the patient's identity. As another example, the healthcare professional may confirm the patient's identity based on a wristband the patient is wearing. Such external confirmation of the patient's identity may lead to errors.

SUMMARY OF THE INVENTION

One embodiment is a device for displaying injection sites of patients. This embodiment may comprise: a display configured to display medical information of a patient; and a processor configured to: receive vein patterns of the patient; determine an identity of the patient based on the vein patterns; display a graphical indicia of a previous injection site of the patient on the display; and display a graphical indicia of a potential new injection site for the patient on the three-dimensional avatar, wherein the position of the previous injection site of the patient and the position of the potential new injection site for the patient do not overlap.

Another embodiment is a method for medical workflow compliance. This embodiment may comprise: receiving vein patterns of a patient; determining an identity of the patient based on the vein patterns; displaying a procedure to be performed for the patient based on the identity of the patient; capturing a performance of the procedure; and confirming the procedure is properly performed.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Overview

Disclosed herein are systems and methods for graphically displaying previous injection sites of a patient to a healthcare professional using computer-generated graphical indicia. In one embodiment, a camera with infrared light capturing capability is used to detect the presence of veins in a patient's extremity or other body areas. The camera can be used for easily detecting the size and position of a vein for blood sample collection or catheter placement. The systems and methods disclosed herein can also be useful for identifying difficult veins and dehydrated patients. The patient's prior injection sites and vein patterns can be stored and retrieved from an electronic medical record system (EMRS). Those sites can then be associated with a graphical indicia that is projected, or viewed through goggles, on a patient's skin. The system can also determine and display one or more potential new injection sites for the patient based on the patient's stored previous injection sites. The displayed potential new injection sites can guide needle insertion into a patient's vein to improve workflow of the healthcare professional. As used herein, a healthcare professional can refer to a physician, nurse, healthcare provider, healthcare administrative staff, or hospital administrator that can operate or make use of the systems and methods disclosed herein.

The prior injection sites and the potential new injection sites may be viewed when a healthcare professional wears a special headset or looks at a specially produced display. The headset may be a 3D visor, such as the Hololens® from Microsoft®, or similar device. Alternatively, the headset may be a custom set of glasses worn by the healthcare professional. The headset can be configured to display graphical indicia of injection sites as appearing overlaid on the patient's veins. The previous injection sites can be locations of prior injections or blood draws. The system can display information associated with the previous injection sites, such as when previous injections or blood draws were performed. The system can determine and record actual new injection sites of injections or blood draws using an imaging sensor that records where and when a new injection is performed on a patient. The performance of an injection or blood draw can be stored in an electronic medical record system, which becomes part of a patient's medical record.

Prior to retrieving the patient's prior injection sites for displaying, a medical information system (MIS) can determine the patient's identity based on the patient's vein pattern. This identification scheme may also be referred to as vein authentication. The patient's vein pattern can be captured by an infrared (IR) imaging sensor because hemoglobin in the veins will absorb IR light. The patient's identity can then be determined based on the unique pattern of the captured veins. Patient identification using vein authentication does not depend on verbal confirmation by the patient, so the patient does not need to be awake or conscious to be identified. In addition, identification does not require scanning a barcode on a patient wristband.

Improper patient identification can result in medication and diagnostic errors. Improving patient identification using vein authentication, while adding in sample collection, can reduce pain to the patient from repeated needle pricks and increase patient safety by ensuring the right sample is collected from the right patient during sample collection. Furthermore, nurse training and quality of care can be measured and improved. For example, the number of times a patient is injected, and the duration of a sample collection, can be determined and analyzed.

A medical information system (MIS) can be used to ensure that the medical processes are compliant with specific medical workflows. For example, a doctor may order an injection of a drug for a patient. Based on the type of injection, the drug, and the patient's physical characteristics (e.g., height, weight, or age), the medical information system can determine the proper syringe size and needle size. The headset or display can display the proper syringe size, needle size and drug to a healthcare professional preparing the injection. A camera can capture and authenticate that the healthcare professional has chosen the correct syringe, needle, and drug for the injection and store that information in the medical record.

Displaying, Determining, and Recording Injection Sites

Figure 1:
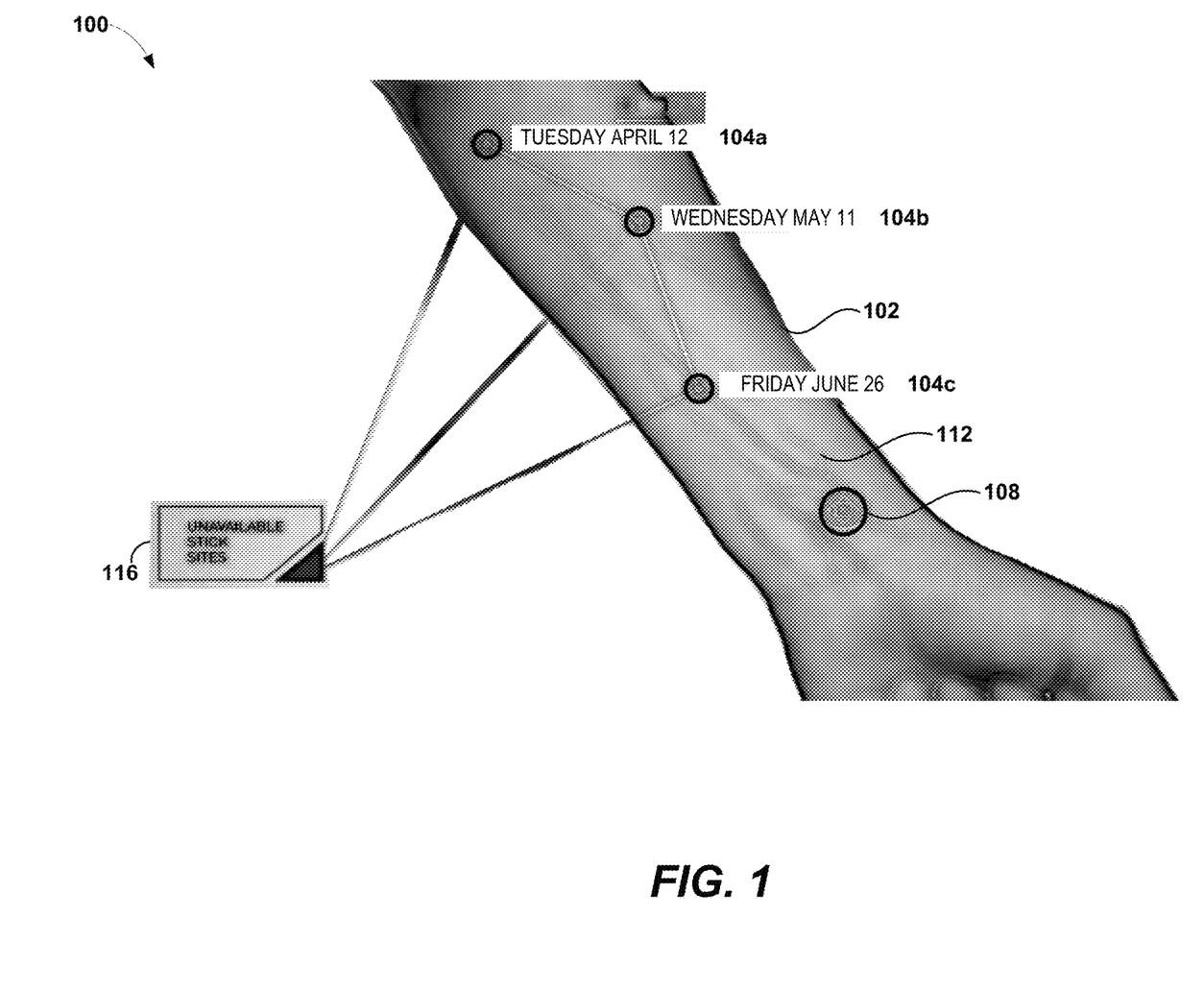
FIG. 1 is a schematic illustration showing exemplary unavailable previous injection sites on the arm of a patient indicated by projected graphical indicia and a potential new injection site shown as a new graphical indicia overlaid on the patient's arm.

FIG. 1 is a schematic illustration showing a patient's arm 102 having a series of veins 112. Also shown are previous injection sites 104a-104c which indicate the positions in the veins 112 where prior injections have occurred. A potential new injection site 108 in the arm 102 is also shown as overlaid on the patient's veins 112. To retrieve the patient's prior injection sites 104a-104c for displaying, a medical information system (MIS) can determine the patient's identity based on the patient's vein pattern 112 (also referred to as vein authentication). The patient's vein pattern 112 can be captured by an infrared (IR) camera because of hemoglobin absorption of IR light. The patient's prior injection sites 104a-104c and vein pattern 112 can be stored and retrieved from an electronic medical record system (EMRS) (such as the electronic medical record system 210 in FIG. 2). The MIS can also determine and display one or more potential new injection sites 108 for the patient based on the patient' previous injection sites 104a-104c.

The prior injection sites 104a-104c and the potential new injection sites 108 can be viewed when a healthcare professional wears a special headset, or looks at a specially produced display. One type of special headset is holographic eyewear. The holographic eyewear can include an infrared (IR) camera for capturing the patient's vein pattern 112 for vein authentication. The special headset can be configured to display injection sites 104-104c as appearing to be graphical indicia overlaid on the patient's veins. The previous injection sites 104a-104c can be locations of prior injections or blood draws. The system can display various types of information associated with the previous injection sites 104a-104c, such as when previous injections or blood draws were performed. In FIG. 1, the injection sites 104a-104c are displayed with their injection or blood draw dates of Tuesday April, Wednesday May 11, and Friday June 26 respectively. The system can display an information item 116 common to all the injection sites 104a-104c. In FIG. 1, the information item 116 shows that the injection sites 104a-104c are unavailable sites for injections or blood draws.

A healthcare professional may perform an injection or blood draw at the potential new injection site 108 determined by the system. The system can determine and record the actual new injection or blood draw site when the healthcare professional performs the procedure. For example, the system can determine the position of the new injection site when the needle comes into contact with the patient's arm. As another example, the health care professional can give the system a command that the actual injection site used will be the injection site 108 suggested by the system.

System Overview

Figure 2:
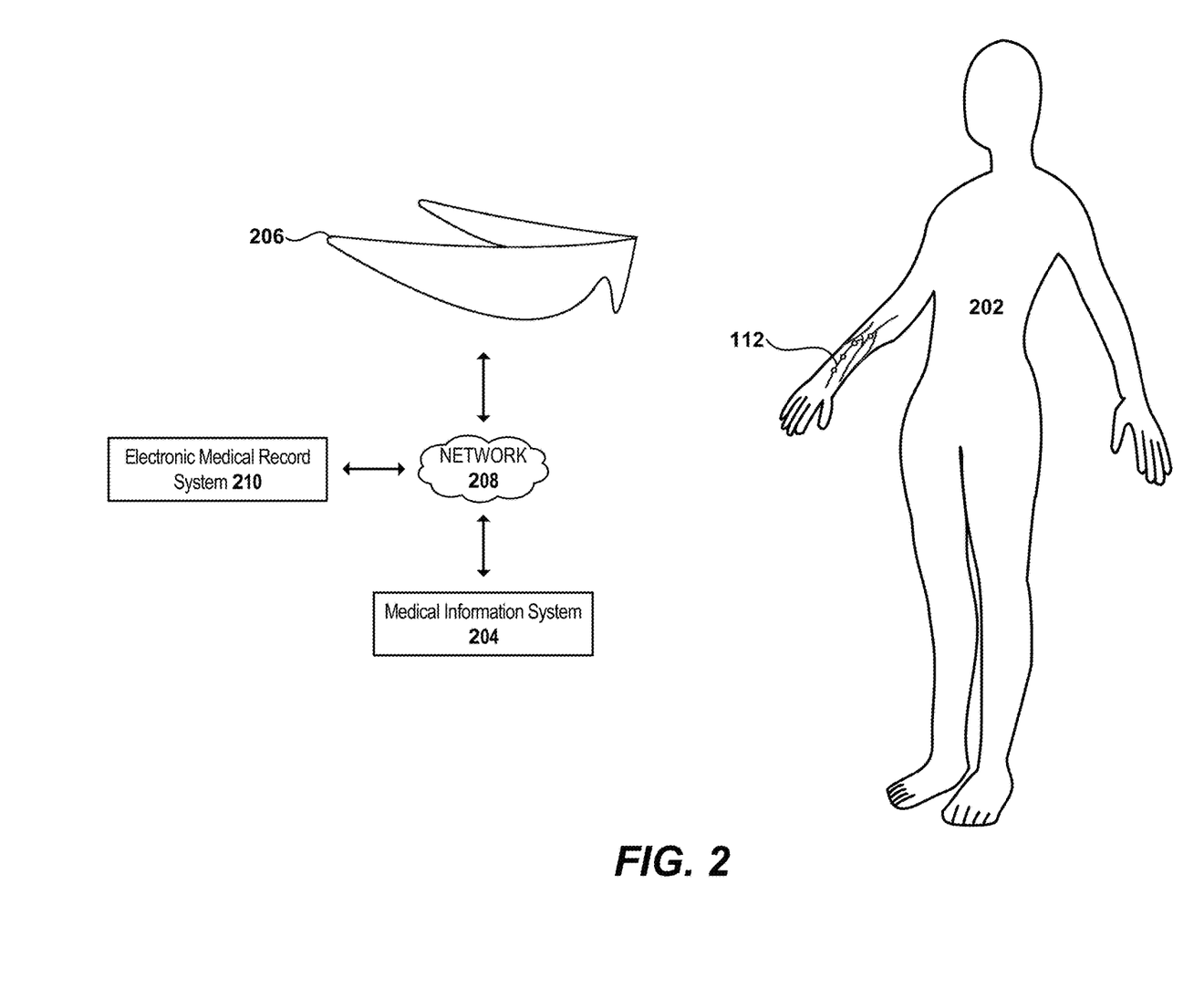
FIG. 2 is a schematic illustration showing exemplary interactions between a holographic eyewear, a medical information system, and an electronic medical record system.

FIG. 2 is a schematic illustration showing exemplary interactions between a headset 206, a medical information system 204, and an electronic medical record system 210. A healthcare professional can interact with the medical information system 204 using a headset 206 that is configured to display 3D representations of the avatar or other information such as injection sites. Microsoft® HoloLens® is a non-limiting example of one type of headset or holographic eyewear that may be used within embodiments of the invention. Other non-limiting examples of headsets or holographic eyewear include Google® Glass®, Oculus® Rift®, Sony® Glasstron®, and HTC® Vive®.

The holographic eyewear 206 generally includes two lenses, one for each of the healthcare professional's eyes, that can present a 3D image within the healthcare professional's field of view. The holographic eyewear 206 can display information, such as the previous injection sites 104a-104b and potential injection sites 108 of a patient 202, to the healthcare professional via its two lenses. In some embodiments, the holographic eyewear 206 can communicate with the healthcare professional using its one or more speakers or earphones.

The holographic eyewear 206, its one or more sensors, is configured to monitor and determine the healthcare professional's commands (such as the location of an actual new injection site). The healthcare professional can give commands read by the holographic eyewear 206 using the movements of fingers, hands, arms, legs or other objects connected with the healthcare professional. The holographic eyewear 206 can be in communication with a medical information system 204 through a network 208.

The medical information system 204 can be configured to retrieve medical information, for example previous injection sites 104a-104c, from an electronic medical record system (EMRS) 210 for display by the holographic eyewear 206 to the healthcare professional. The previous injection sites 104a-104c retrieved from the electronic medical record system 210 can be captured and created by the holographic eyewear 206 and the medical information system 204. In some embodiments, the previous injection sites retrieved from the electronic medical record system 210 can be captured and created by systems other than the holographic eyewear 206 and the medical information system 204. The patient's previous injection sites 104a-104c can be displayed as being overlaid on the patient's veins 112.

In some embodiments, the headset can be configured to display injection sites as appearing overlaid on a three-dimensional (3D) or a two-dimensional (2D) avatar instead of on the patient. The avatar may represent a human body in three dimensions. The 3D or 2D avatar can be a holographic avatar. Non-limiting examples of technologies for implementing the methods and systems disclosed herein include mixed reality technology, augmented reality technology, and virtual reality technology.

Method for Determining and Displaying a Potential New Need Site

Figure 3:
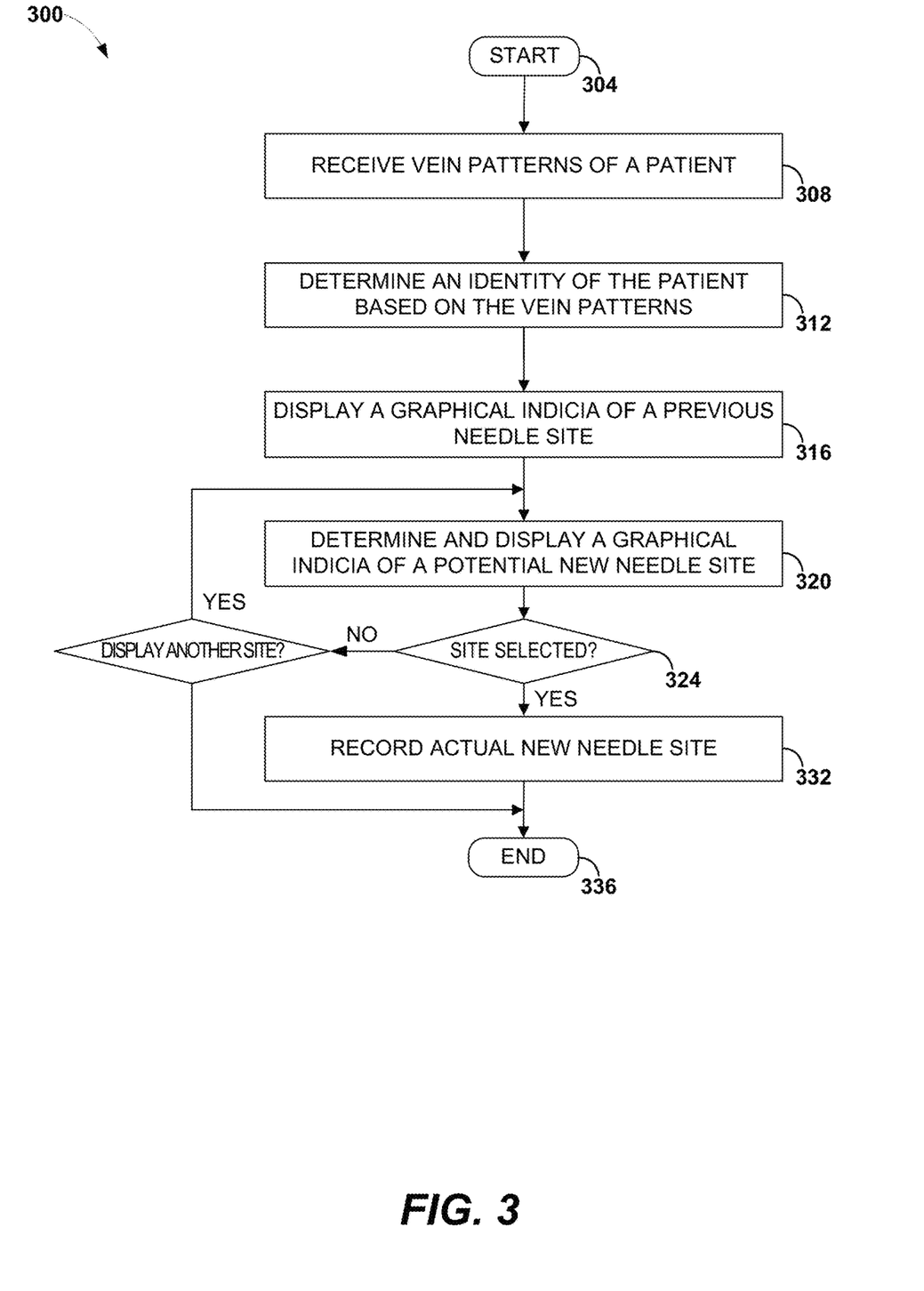
FIG. 3 is a flow diagram depicting an illustrative method for determining and displaying a potential new injection site based on the location of a previous injection site.

FIG. 3 is a flow diagram depicting an illustrative method 300 for determining and displaying a potential new injection site based on the location of a previous injection site. After beginning at a start block 304, the method 300 running in a medical information system receives vein patterns of a patient at block 308. For example, a headset can include an infrared (IR) sensor for capturing the vein patterns of the patient.

The process 300 then moves to a block 312, to determine an identity of the patient based on the captured vein patterns from the patient. The captured vein patterns of the patient can be compared with an electronically stored vein pattern template of the patient. In one example, the vein pattern template can be retrieved from an electronic medical record system (EMRS) via a medical information system (MIS). By comparing the captured vein patterns and the retrieve vein pattern template, the method 300 determines and confirms the identity of the patient. One method of doing vein pattern matching can be found in U.S. Pat. No. 6,301,375 which is hereby incorporated by reference in its entirety.

The process 300 then moves to a block 316, wherein the system can display a graphical indicia of a previous injection site. For example, the system can display a graphical indicia of a previous injection site on a headset. To the healthcare professional wearing the headset, the graphical indicia can appear as overlaid on the patient at a position that corresponds to the position of the previous injection site. The graphical indicia can be a circle, square, rectangle, or any other geometric shape that indicate the position of an injection site. The system can retrieve the position of the previous injection site from an electronic medical record system via a medical information system. In some embodiments, the system can display the graphical indicia of the previous injection site on a three-dimensional (3D) avatar. The graphical indicia can be at a position that corresponds to the position of the previous injection site of the patient.

The method 300 then moves to a block 320 to display a graphical indicia of a potential new injection site. To the healthcare professional wearing a headset, the graphical indicia can appear as overlaid on the patient at a position that corresponds to the position of the potential new injection site. The graphical indicia can be any shape that indicates a position of an injection site. In some embodiments, the system can display the graphical indicia of the potential new injection site on a three-dimensional (3D) avatar. In one embodiment, the system can determine the position of the potential new injection site based on the position of the previous injection site. For example, the position of the previous injection site of the patient and the position of the potential new injection site for the patient may not overlap.

The process 300 then moves to a decision block 324, wherein a determination is made whether a healthcare professional has selected the potential new injection site. For example, a determination is made that a healthcare professional has selected the potential new injection site after receiving an instruction from the healthcare professional selecting the potential new injection site for the injection. The healthcare professional may make this instruction by making a software selection, or using a holographic projection on the headset to choose a particular indicator. If the healthcare professional has not selected the potential new injection site, the method 300 proceeds to a decision block 328, where the system determines whether the healthcare professional would like for a different potential new injection site to be displayed. If the healthcare professional makes a selection that a different potential new injection site should be displayed, the method 300 returns to block 320. If the healthcare professional indicates that he or she does not want a different potential new injection site displayed, the method proceeds to an end block 336, where the method 300 ends.

At decision block 324, if the healthcare professional has selected a potential new injection site, the method 300 proceeds to a block 332, where the system determines and records the position of the actual new injection site for the patient. For example, the actual new injection site of the patient is determined when the user indicates the actual new injection site on the patient. As another example, the new injection site is determined when the headset determines that a syringe has come into contact with the patient. As a further example, the new injection site of the patient may be determined when the user indicates a position on the 3D avatar that corresponds to the actual new injection site. The electronic medical record system can store the position of the actual new injection site for the patient. The electronic medical system can also store a procedure such as an injection or blood draw as an image or a video, which can be part of the patient's medical record.

Method for Workflow Compliance

Figure 4:
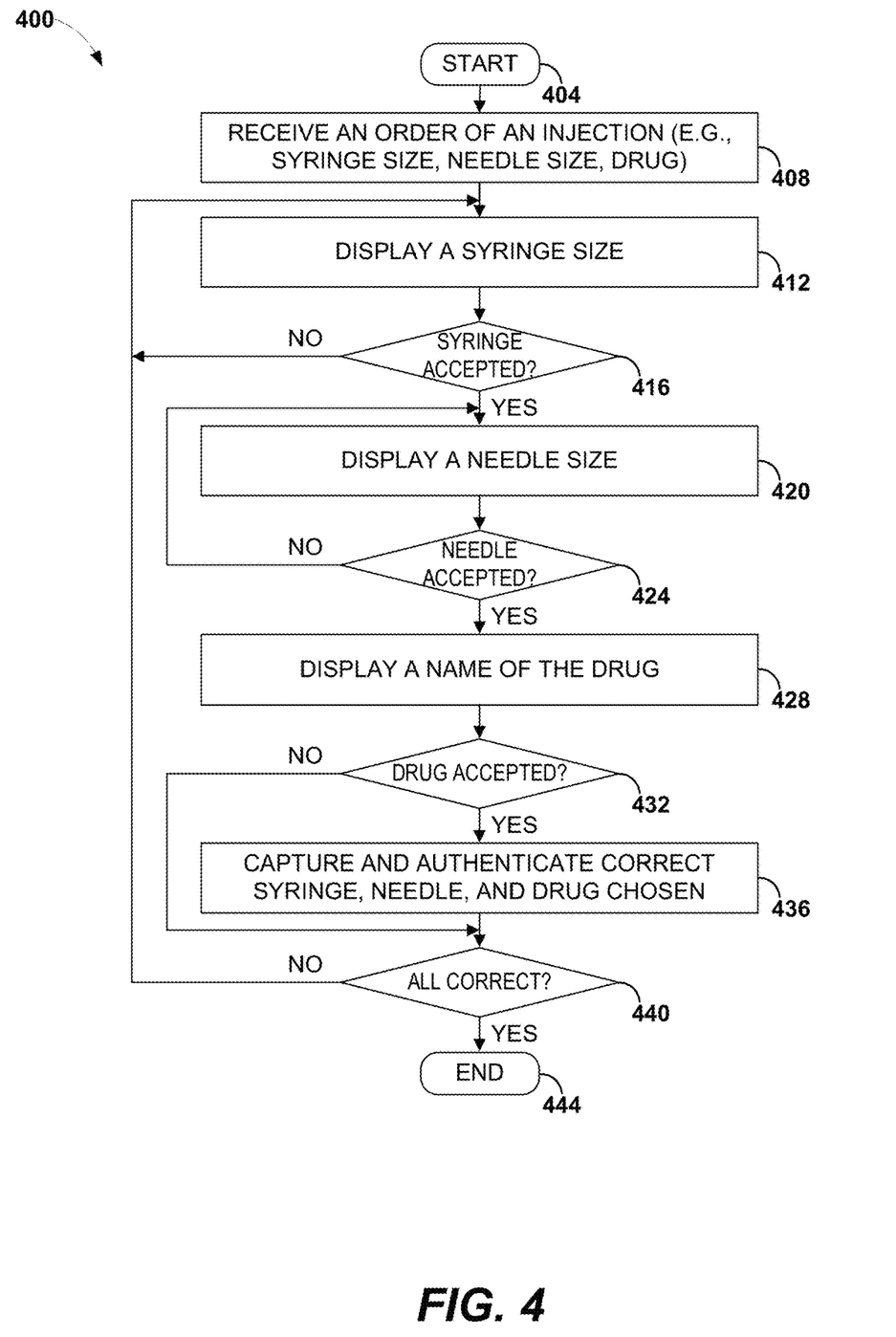
FIG. 4 is a flow diagram depicting an illustrative method for injection workflow compliance.

FIG. 4 is a flow diagram depicting an illustrative method 400 running in a medical information system for injection workflow compliance. After the method 400 begins at a start block 404, the method 400 receives an order of an injection (or another procedure such as blood draw) for a patient. The order can be based on the identity of the patient. The identity of the patient can be determined based on vein authentication. For example, the vein patterns of the patient can be compared to a vein pattern template of the patient to confirm the identity of the patient.

The method 400 then moves to a block 412, wherein the system displays a proper syringe size for the injection. A headset used by the healthcare provider can display the proper syringe size to the healthcare professional based on the patient's medical record and any pharmacy orders. At a decision block 416, the system receives a command from a healthcare professional whether he or she has accepted the displayed syringe size. If the healthcare professional has not accepted the displayed syringe size, the method 400 returns to block 412. If the healthcare professional has accepted the displayed syringe size, the method 400 proceeds to a block 420.

At block 420, the system displays a proper needle size for the injection. A headset 206 can display the proper needle size to the healthcare professional. Based on the type of injection, the drug, and the patient's physical characteristics (e.g., height, weight, or age), the method 400 can determine the proper syringe size and needle sizes. There may be multiple combinations of proper syringe and needle sizes. At decision block 424, the method 400 receives a command from the healthcare professional whether he or she has accepted the displayed needle size. If the healthcare professional has not accepted the displayed needle size, the method 400 proceeds to block 420. If the healthcare professional has accepted the displayed needle size, the method 400 proceeds to block 428.

At block 428, the method 400 displays a name of the drug to be administered. A headset can display the drug name to the healthcare professional. At a decision block 432, the method receives a command from the healthcare professional whether he or she has accepted the displayed drug for administering. If the healthcare professional has not accepted the displayed drug, the method 400 ends at an end block 444. If the healthcare professional has accepted the displayed drug, the method 400 proceeds to a block 436.

At block 436, system captures and authenticate that the correct syringe, needle, and drug have been used by the healthcare professional for the injection. For example, the system can capture a performance of the procedure and confirm that the procedure is property performed. For example, a syringe or its package can have a barcode. The system can determine that a proper syringe has been used by the healthcare professional to prepare the injection by capturing an image of the syringe or the syringe's package to capture the barcode. As another example, a bottle of the drug can include a barcode on its label. The system can determine that a correct drug has been used by the healthcare professional to prepare the injection by capturing an image of the bottle's label to capture the barcode. The performance of the procedure or injection can be stored in the electronic medical record system, which can be part of the patient's medical record. If the method 400 determines at a decision block 440 that the syringe, needle, and drug used by the healthcare professional are correct, the method 400 ends at end block 444. At decision block 440, if the method determines that an incorrect syringe, needle, or drug has been used by the healthcare professional in preparing an injection, the method returns to block 412.

Operating Environment

Holographic Eyewear

Figure 5:
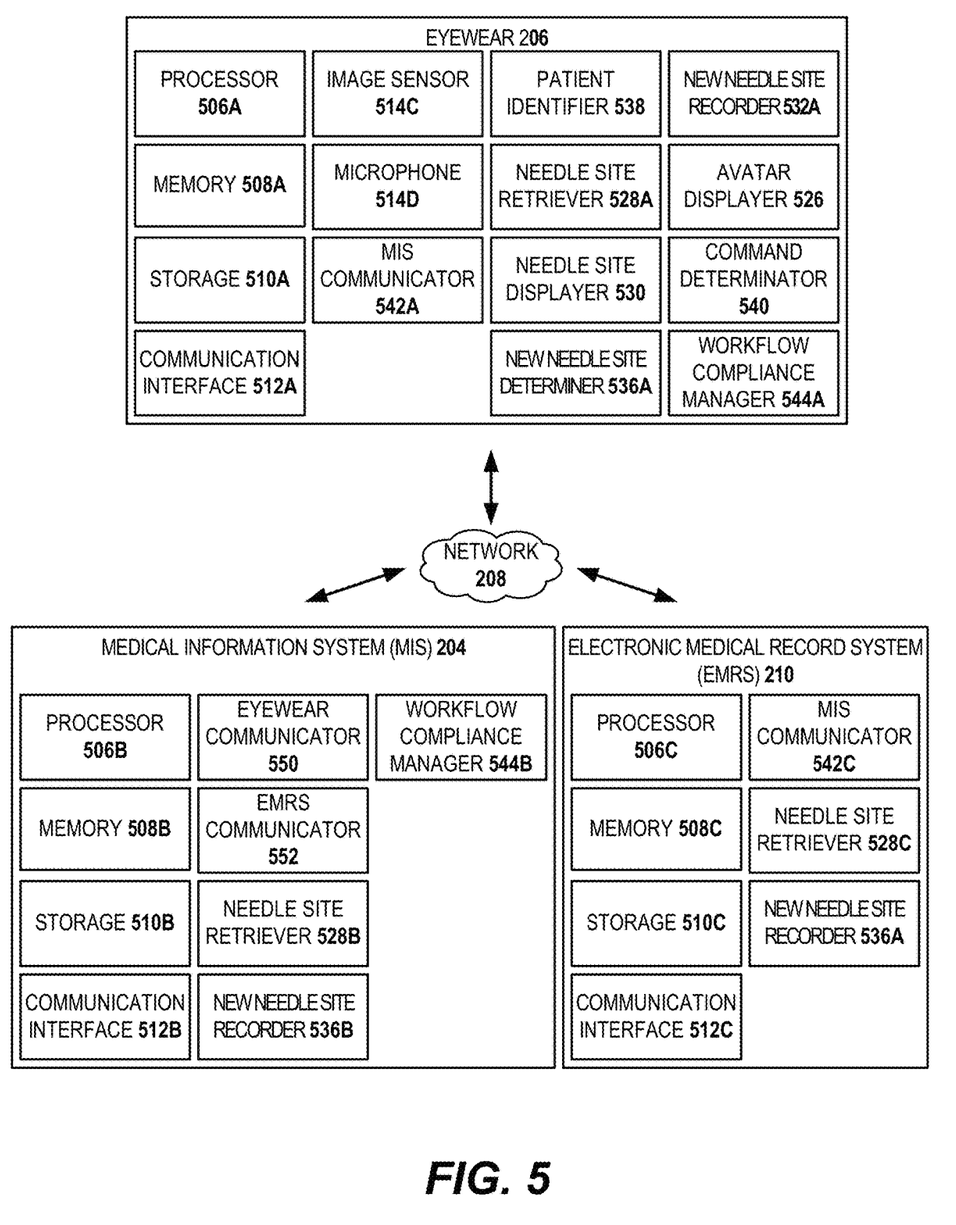
FIG. 5 is a block diagram depicting an illustrative operating environment of a holographic eyewear, a medical information system, and an electronic medical record system.

FIG. 5 is a block diagram depicting an illustrative operating environment of a headset 206, a medical information system 204, and an electronic medical record system 210. While many configurations are possible for the headset 206, an embodiment of the headset 206 is illustrated in FIG. 5. As illustrated, the headset 206 can include a processor 506A that is in electrical communication with a memory 508A, a storage 510A, and a communication interface 512A. The memory 508A stores instructions for configuring the processor 506A to perform the functions of the headset 206 when the headset 206 is powered on. When the headset 206 is powered off, the storage 510A stores instructions for configuring the processor 506A to perform the functions of the headset 206. The communication interface 512A facilitates the communications between the headset 206 and other devices connected to the network 208, for example the medical information system 204.

The headset 206 can include one or more sensors such as an image sensor 514C (such as an infrared (IR) imaging sensor) or a microphone 514D in electrical communication with the processor 506A. These sensors may be configured to detect the healthcare professional's movements and the sounds he makes, for example what he provides verbal commands to the headset 206. These sensors can detect the movements of people and objects the healthcare professional sees through the lenses of the headset 206. A medical information system (MIS) communicator 542A and the communication interface 512A are configured to facilitate the communication between the headset 206 and the medical information system 204.

The patient identifier 538 is configured to determine the identity of a patient based on the vein patterns of the patient captured by the image sensor 512C of the headset 206. The headset 206 can include an injection site retriever 528A, an injection site displayer 530, a new injection site recorder 532A, and a new injection site determiner 536A. The injection site retriever 528A is configured to retrieve prior injection sites from the electronic medical record system 210. The injection site displayer 530 is configured to display previous injection sites and potential new injection sites to the healthcare professional. The new injection site recorder 532A is configured to determine and record actual new injection sites for storage in the electronic medical record system 210. The new injection site determiner 536A is configured to determine potential new injection sites based on prior injection sites of the patients.

The headset 206 can include an avatar displayer 526 configured to display a 3D avatar to a healthcare professional. A command determiner 540 of the headset 206 is configured to determine the commands given by the healthcare professional to the headset 206 based on the one or more sensors. A workflow compliance manager 544A of the headset 206 is configured to ensure workflow compliance (e.g., the method 400 for injection workflow compliance illustrated in FIG. 4).

Medical Information System

While many configurations are possible for the medical information system 204, an embodiment of the medical information system 204 is illustrated in FIG. 5. As illustrated, the medical information system 204 can include a processor 506B that is in electrical communication with a memory 508B, a storage 510B, and a communication interface 512B. The memory 508B stores instructions to configure the processor 506B to perform the functions of the medical information system 204 when the medical information system 204 is powered on. When the medical information system 204 is powered off, the storage 510B stores the instructions for configuring the processor 506B to perform the functions of the medical information system 204. The communication interface 512B facilitates the communications between the medical information system 204 and other devices connected to the network 208, for example the headset 206 and the electronic medical record system 210.

An eyewear communicator 550 of the medical information system 204 and the communication interface 512B are configured to facilitate the communication between the medical information system 204 and the headset 206. An electronic medical record system communicator 552 of the medical information system 204 and the communication interface 512B are configured to facilitate the communication between the medical information system 204 and the electronic medical record system 210.

The headset 206 can include one or more of an injection site retriever 528B, a new injection site recorder 532B, and a new injection site determiner 536B. The injection site retriever 528B is configured to retrieve previous injection sites of patients stored in the electronic medical record system 210. The new injection site recorder 532B is configured to determine new injection sites for storage in the electronic medical record system 210. The new injection site determiner 536B is configured to determine potential new injection sites for patients based on patients' previous injection sites.

The medical information system 204 can include a workflow compliance manager 544B is configured to determine the appropriate instructions the healthcare professional should follow under various circumstances, such as the proper syringe size, needle sizes, and drugs for injections.

Electronic Medical Record System

While many configurations are possible for the electronic medical record system 210, an embodiment of the electronic medical record system 210 is illustrated in FIG. 5. As illustrated, the electronic medical record system 210 can include a processor 506C that is in electrical communication with a memory 508C, a storage 510C, and a communication interface 512C. The memory 508C stores instructions to configure the processor 506C to perform the functions of the electronic medical record system 210 when the electronic medical record system 210 is powered on. When the electronic medical record system 210 is powered off, the storage 510C stores the instructions for configuring the processor 506C to perform the functions of the electronic medical record system 210. The storage 510C can also store patient medical records. The communication interface 512C facilitates the communications between the electronic medical record system 210 and other devices connected to the network 208, for example the medical information system 204.

The headset 206 can include one or more of an injection site retriever 528C, and a new injection site recorder 532C, and the medical information system communicator 542C. The injection site retriever 528C is configured to retrieve medical records stored in the storage 510C of the electronic medical record system 210. The new injection site recorder 532C is configured to create medical records for storage in the storage 510C of the electronic medical record system 210. The medical information system communicator 542C and the communication interface 512C are configured to facilitate the communication between the electronic medical record system 210 and the medical information system 204.

In some embodiments, the medical information system 204 can perform some of the functions of the headset 206. In some embodiments, the headset 206 can perform some of the functions of the medical information system 204. In some embodiments, the medical information system 204 can perform some of the functions of the electronic medical record system 210. In some embodiments, the electronic medical record system 210 can perform some of the functions of the medical information system 204.

The medical information system 204 and the headset 206 can communicate with each other through the network 208 using the communication interface 512A or 512B respectively. The medical information system 204 and the electronic medical record system 210 can communicate with each other through the network 208 using the communication interface 512B or 512C respectively. The communication interface 512A, 512B, or 512C can be connected to the network 208 by wired or wireless communications, cellular communication, Bluetooth®, local area network (LAN), wide local area network (WLAN), radio frequency (RF), infrared (IR), or any other communication method or system known in the art. In some embodiments, the communication interface 512A, 512B, or 512C communicates with one another using cloud connectivity. The medical information system 204 can send data to and receive data from the headset 206 using the communication interface 512A or 512B, medical information system communicator 542A and the eyewear communicator 550. The medical information system 204 can send data to and receive data from the electronic medical record system 210 using the communication interface 512B or 512C and the electronic medical record system communicator 552 and the medical information system 544C.

Sensors

The headset 206 can include, for example, two image sensors 514C. The two image sensors 514C enable the headset 206 to capture what the healthcare professional sees. One of the two image sensors 514C can be located spatially near the left eye of the healthcare professional and be oriented such that it captures what the healthcare professional's left eye sees. The other of the two image sensors 514C can be located spatially near the right eye of the healthcare professional and be oriented such that it detects what the healthcare professional's right eye sees. In some embodiments, the two image sensors 514C convert photons into electrical signals and images for processing by the command determiner 540. In some embodiments, the headset 206 can combine, using the processor 506A and the memory 508A, the images from the two image sensors 514C to create stereoscopic images of what the healthcare professional sees with his two eyes. In some embodiments, the headset 206 can include one image sensor 514C. The image sensor 514C can be located between the two eyes and be oriented such that it detects and approximates what the healthcare professional sees with his two eyes. In some embodiments, the image sensor 514C can be located at other locations on the headset 206.

The headset 206 can capture what the healthcare professional sees in his field of view using the one or more image sensors 514C. In some embodiments, the headset 206 can detect more or less than what the healthcare professional sees in his field of view using the one or more image sensors 514C. As illustrated with reference to FIG. 2, when the healthcare professional sees, through the headset 206, that one or more of his fingers, hands, arms, legs, or one or more objects he is connected with, come into contact with a content item, the headset 206 can determine that such a contact has occurred. The headset 206, using the one or more image sensors 514C, can determine that such a contact has occurred. Consequently, the headset 206 can capture and "see" the commands that the healthcare professional gives to the headset 206 using his fingers, hands, arms, legs, or one or more objects he is connected with. In some embodiments, the headset 206 can create a new video medical record or a new image medical record using the one or more image sensors 514C.

The microphone 514C can be configured to detect sound from the environment surrounding the headset 206 and from the healthcare professional. The headset 206 detects and "hears" what the healthcare professional hears and says. In some embodiments, the microphone 514C converts acoustic waves into electrical signals for processing by the command determiner 540.

Avatar Display

The headset 206 can include the avatar displayer 526 in communication with the processor 506A. The avatar displayer 526 determines the characteristics of the 3D avatar 202 shown to the healthcare professional on the one or more lenses of the headset 206. Non-limiting examples of the characteristics of the 3D avatar 202 include color, opacity, size, orientation, and location. In some embodiments, the avatar displayer 526 can determine the size of the 3D avatar 202 based on the weight and height of the patient. The avatar displayer 526 can determine the size of the 3D avatar 202 based on, for example, the number and the sizes of the various content items the one or more lenses of the headset 206 shows to the healthcare professional. The avatar displayer 526 can determine the location of the 3D avatar 202 based on, for example, the colors, opacities, sizes, orientations, and locations of other objects in the holographic eyewear's field of view. Non-limiting examples of other objects include patients, doctor office furniture, and medical instruments. For example, the avatar displayer 526 can display the 3D avatar 202 on the one or more lenses of the headset 206 such that the 3D avatar 202 coincide with or overlap the patient. As another example, the avatar displayer 526 can display the 3D avatar 202 on the one or more lenses of the headset 206 such that the 3D avatar 202 is adjacent to the patient.

Injection Site Retrieval, Display, Determination, and Recording

The headset 206 can include one or more of the injection site retriever 528A, the injection site displayer 530, the new injection site recorder 532A, and the new injection site determiner 536A in communication with the processor 506A. The injection site retriever 528A, in conjunction with the injection site retriever 528B of the medical information system 204 and the injection site retriever 528C of the electronic medical record system 210, can retrieve previous injection sites stored in the electronic medical record system 210. To retrieve the previous injection sites stored in the electronic medical record system 210, the injection site retriever 528A can send one or more requests for previous injection sites to the injection site retriever 528B of the medical information system 204. Based on the identity of the patient, for example, determined by the patient identifier 538, the injection site retriever 528B can retrieve the requested injection sites from the injection site retriever 528C of the electronic medical record system 210. The injection site retriever 528B then can send the requested injection sites retrieved from the electronic medical record system 210 to the headset 206.

The injection site displayer 530 can display previous and potential new injection sites. The injection site displayer 530 can display injection sites as overlaid at locations of the actual injection sites on the patient 202. In some embodiments, the injection site displayer 530 can display some or all of the previous injection sites retrieved from the electronic medical record system 210 to the healthcare professional.

Referring to FIG. 5, the new injection site recorder 532A, in conjunction with the new injection site recorder 532B of the medical information system 204 and the new injection site recorder 532C of the electronic medical record system 204, enables storing new injection sites. The electronic medical record system 210 can store new injection sites in the storage 510C. The new injection site determiner 536A is configured to determine potential new injection sites based on prior injection sites of the patients, such that the injection sites of a patient do not overlap.

Command Determination

The headset 206 can include the command determiner 540 in communication with the processor 506A. The command determiner 540, in conjunction with the one or more sensors of the headset 206, can determine the commands the healthcare professional gives to the headset 206. Thus, the healthcare professional can interact with the headset 206 and the medical information system 204 through the command determiner 540 and the one or more sensors 514.

In some embodiments, the one or more image sensors 514C are located and oriented on the headset 206 such that they can detect what the healthcare professional sees. The headset 206, using the one or more image sensors 514C, can capture and "see" the movements of the healthcare professional's fingers, hands, arms, legs, and one or more objects he is connected with. The command determiner 540, based on the images captured by the one or more image sensors 514C, can determine that these movements are visual commands given by the healthcare professional. Based on the visual commands, the headset 206 can update the display shown to the healthcare professional on its one or more lenses.

In some embodiments, the headset 206, using the one or more microphones 514C, can detect the words that the healthcare professional has said. The command determiner 540, based on the signals produced by the one or more microphones 514C, can determine that the words are verbal commands given by the healthcare professional. Based on the verbal commands, the headset 206 can update the display shown to the healthcare professional.

Instructions in the command determiner 540 can configure the processor 506A to determine the commands by the healthcare professional. In some embodiments, the command determiner 540 can include instructions that configure the processor 506A to interpret and apply one or more filters to the data received from the one or more sensors. For example, the command determiner 540 can include instructions that configure the processor 506A to apply one or more filters to interpret the acoustic waveforms captured by the microphone 514C, for example, to remove noise from the healthcare professional's environment captured by the microphone 514C. Instructions in the command determiner 540 can also configure the processor 506A to extract command parameters from the data received by the one or more sensors.

Workflow Compliance Manager

The headset 206 can include the task workflow displayer 544A in communication with the processor 506A. The medical information system 204 can include the task workflow displayer 544B in communication with the processor 506B. The task workflow displayer 544A, with the task workflow displayer 544B, can determine the appropriate instructions the healthcare professional should follow for a given task. The task workflow displayer 544A can store instructions the healthcare professional should follow for various tasks in the storage 510A. In some embodiments, the task workflow displayer 544B can store instructions the healthcare professional should follow for various tasks in the storage 510B. The task workflow displayer 544B can provide the task workflow displayer 544A with instructions stored for various tasks stored in the storage 510B that the healthcare professional should follow.

For example, to locate veins in a patient's arm for blood draw, the task workflow displayer 544A can display instructions, on the holographic eyewear's one or more lenses, to the healthcare professional that he should follow in order to successfully locate veins in the patient's arm for blood draw. For example, to insert a catheter into a patient, the task workflow displayer 544A can display instructions, on the holographic eyewear's one or more lenses, to the healthcare professional that he should follow in order to successfully insert a catheter into the patient. In some embodiments, the task workflow displayer 544A can display instructions to the healthcare professional to facilitate his compliance with procedures mandated by the hospital, the city, the state, or the federal government.

Communication Between the Eyewear, the Medical Information System, and the Electronic Medical Record System The headset 206 can include the 3D avatar medical information communicator 542A in communication with the processor 506A and the communication interface 512A. The medical information system 204 can include the eyewear communicator 550 in communication with the processor 506B and the communication interface 512B. The 3D avatar medical information communicator 542A and the eyewear communicator 550, together with the communication interface 512A or 512B, facilitate the communication between the headset 206 and the medical information system 204. In some embodiments, the 3D avatar medical information communicator 542A and the eyewear communicator 550, together with the communication interface 512A or 512B, facilitate the communication between the healthcare professional identifier 524A or 524B, the injection site retriever 528A or 528B, the new injection site recorder 532A or 532B, the new injection site determiner 536A or 536B, and the task workflow displayer 544A or 544B.

The medical information system 204 can include the electronic medical record system communicator 552 in communication with the processor 506B and the communication interface 512B. The electronic medical record system 210 can include the 3D avatar medical information communicator 542C in communication with the processor 506C and the communication interface 512C. The electronic medical record system communicator 550 and the 3D avatar medical information communicator 542A, together with the communication interface 512B or 512C, facilitate the communication between the medical information system 204 and the electronic medical record system 210. In some embodiments, the electronic medical record system communicator 550 and the 3D avatar medical information communicator 542A, together with the communication interface 512B/C, can facilitate the communication between the injection site retriever 528B/C, and the new injection site recorder 532B/C.

Each of the processes, methods, and algorithms described herein and/or depicted in the attached figures may be embodied in, and fully or partially automated by, code modules executed by one or more physical computing systems, hardware computer processors, application-specific circuitry, and/or electronic hardware configured to execute specific and particular computer instructions. For example, computing systems can include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some implementations, particular operations and methods may be performed by circuitry that is specific to a given function.

Further, certain implementations of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities can be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto can be performed in other sequences that are appropriate, for example, in serial, in parallel, or in some other manner. Tasks or events may be added to or removed from the disclosed example embodiments. Moreover, the separation of various system components in the implementations described herein is for illustrative purposes and should not be understood as requiring such separation in all implementations. It should be understood that the described program components, methods, and systems can generally be integrated together in a single computer product or packaged into multiple computer products. Many implementation variations are possible.

The processes, methods, and systems may be implemented in a network (or distributed) computing environment. Network environments include enterprise-wide computer networks, intranets, local area networks (LAN), wide area networks (WAN), personal area networks (PAN), cloud computing networks, crowd-sourced computing networks, the Internet, and the World Wide Web. The network may be a wired or a wireless network or any other type of communication network.

The systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure. Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. No single feature or group of features is necessary or indispensable to each and every embodiment.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted can be incorporated in the example methods and processes that are schematically illustrated. For example, one or more additional operations can be performed before, after, simultaneously, or between any of the illustrated operations. Additionally, the operations may be rearranged or reordered in other implementations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A system for displaying injection sites of patients, comprising:
   a display configured to display medical information of a patient; and
   a processor configured to:
      receive vein patterns of the patient;
      determine an identity of the patient based on the vein patterns;
      display a graphical indicia of a previous injection site of the patient on the display; and
      display a graphical indicia of a potential new injection site for the patient, wherein the position of the previous injection site of the patient and the position of the potential new injection site for the patient do not overlap.

2. The system of claim 1, wherein the processor is further configured to receive an indication of the user selecting the potential new injection site for the patient.

3. The system of claim 2, wherein the processor is further configured record the position of the potential new injection site for the patient.

4. The system of claim 1, wherein the system comprises an infrared camera configured to receive the vein patterns of the patient.

5. The system of claim 1, wherein the processor is configured to retrieve the previous injection site from a medical information system.

6. The system of claim 1, wherein the processor is configured to display the graphical indicia of the potential new injection site for the patient based on the position of the previous injection site of the patient.

7. The system of claim 1, wherein the processor is configured to display a three-dimensional (3D) avatar of the patient on the display and the graphical indicia of the previous injection site is overlaid onto the displayed 3D avatar.

8. The system of claim 7, wherein the position of the potential new injection site is displayed on the 3D avatar.

9. The system of claim 1, wherein the display is a headset display and the graphical indicia of the potential new injection site is displayed on the headset to appear overlaid on the patient.

10. The system of claim 1, wherein the system comprises an imaging sensor configured to capture the position of the new injection site.

11. The device of claim 10, wherein the position of the new injection site is determined from the imaging sensor detecting when a syringe comes into contact with the new injection site on the patient.

* * * * *

UNITED STATES PATENT AND TRADEMARK OFFICE
CERTIFICATE OF CORRECTION

PATENT NO. : 10,751,486 B2
APPLICATION NO. : 15/783255
DATED : August 25, 2020
INVENTOR(S) : Yuri Haverman et al.

Page 1 of 1

It is certified that error appears in the above-identified patent and that said Letters Patent is hereby corrected as shown below:

In the Specification

In Column 2, Line 53, delete "Hololens®" and insert -- HoloLens® --.

In Column 3, Line 63, delete "104-104c" and insert -- 104a-104c --.

In the Claims

In Column 16, Line 54, Claim 11, delete "device" and insert -- system --.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*